(12) United States Patent
Sterling et al.

(10) Patent No.: US 8,167,829 B2
(45) Date of Patent: May 1, 2012

(54) ORTHOTIC APPARATUS

(75) Inventors: Shane Sterling, Seattle, WA (US); Jay Bublitz, Shoreline, WA (US)

(73) Assignee: Bellacure Inc., Seattle, WA (US)

( * ) Notice: Subject to any disclaimer, the term of this patent is extended or adjusted under 35 U.S.C. 154(b) by 917 days.

(21) Appl. No.: 11/975,542

(22) Filed: Oct. 19, 2007

(65) Prior Publication Data

US 2009/0105622 A1    Apr. 23, 2009

(51) Int. Cl.
*A61F 5/00* (2006.01)
(52) U.S. Cl. .................. 602/16; 602/20; 602/23; 602/26
(58) Field of Classification Search ................ 602/5, 16, 602/26, 20, 23, 27
See application file for complete search history.

(56) References Cited

U.S. PATENT DOCUMENTS

| | | | |
|---|---|---|---|
| 3,387,305 A * | 6/1968 | Shafer | 2/22 |
| 4,198,708 A * | 4/1980 | Fugere et al. | 2/16 |
| 4,381,768 A * | 5/1983 | Erichsen et al. | 602/16 |
| D298,568 S * | 11/1988 | Womack et al. | D24/190 |
| 5,263,923 A | 11/1993 | Fujimoto | |
| 5,277,698 A | 1/1994 | Taylor | |
| 5,458,565 A | 10/1995 | Tillinghast, III et al. | |
| 5,562,605 A | 10/1996 | Taylor | |
| 5,743,865 A | 4/1998 | Townsend | |
| 5,797,864 A | 8/1998 | Taylor | |
| 5,807,294 A | 9/1998 | Cawley et al. | |
| 6,186,970 B1 | 2/2001 | Fujii et al. | |
| 6,875,187 B2 | 4/2005 | Castillo | |
| 6,994,682 B2 | 2/2006 | Bauerfeind et al. | |
| 7,198,610 B2 | 4/2007 | Ingimundarson et al. | |
| 7,229,390 B2 | 6/2007 | Fujii et al. | |
| 2006/0135900 A1 | 6/2006 | Ingimundarson et al. | |
| 2006/0135901 A1 | 6/2006 | Ingimundarson et al. | |
| 2006/0135902 A1 | 6/2006 | Ingimundarson et al. | |
| 2006/0135903 A1 | 6/2006 | Ingimundarson et al. | |
| 2006/0135904 A1 | 6/2006 | Ingimundarson et al. | |
| 2006/0200057 A1* | 9/2006 | Sterling | 602/5 |
| 2007/0083136 A1 | 4/2007 | Einarsson | |
| 2007/0213648 A1 | 9/2007 | Ferrigolo et al. | |

OTHER PUBLICATIONS

International Searching Authority, International Search Report, mailed on Feb. 26, 2009 for International Application No. PCT/US2008/077234 filed on Sep. 22, 2008.
International Searching Authority, Written Opinion of the International Search Authority, mailed on Feb. 26, 2009 for International Application No. PCT/US2008/077234 filed on Sep. 22, 2008.

* cited by examiner

*Primary Examiner* — Kim Lewis
(74) *Attorney, Agent, or Firm* — Workman Nydegger

(57) ABSTRACT

In one embodiment of the invention, an orthotic apparatus includes a frame structure having an upper frame portion moveable relative to a lower frame portion. The orthotic apparatus further includes at least one strap attached to the upper frame portion and the lower frame portion of the frame structure. The at least one strap and the frame structure, together, are configured to apply a therapeutic moment to a joint of a limb responsive to positioning the limb within a limb-receiving space formed between the at least one strap and the frame structure.

25 Claims, 7 Drawing Sheets

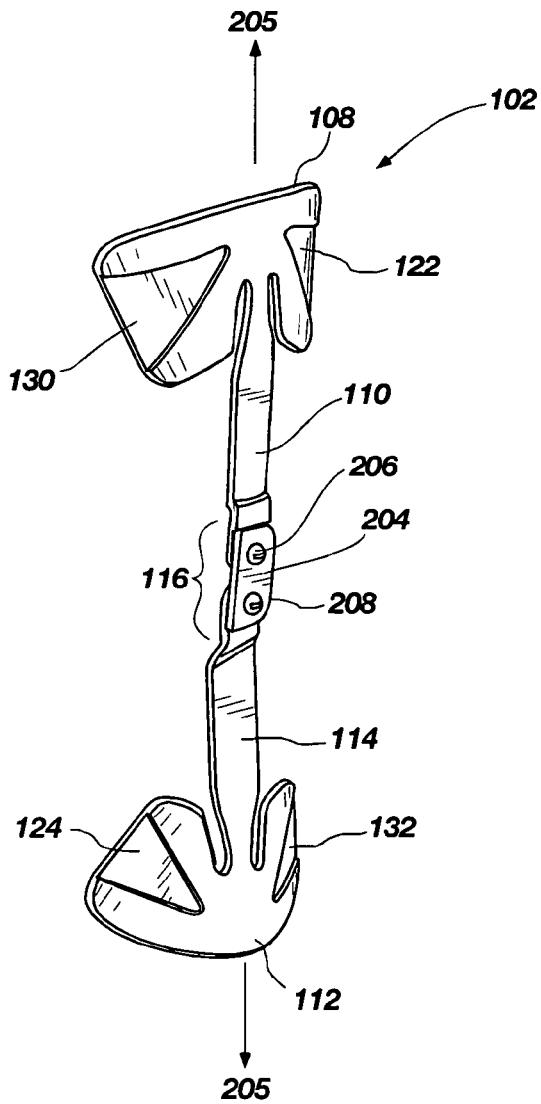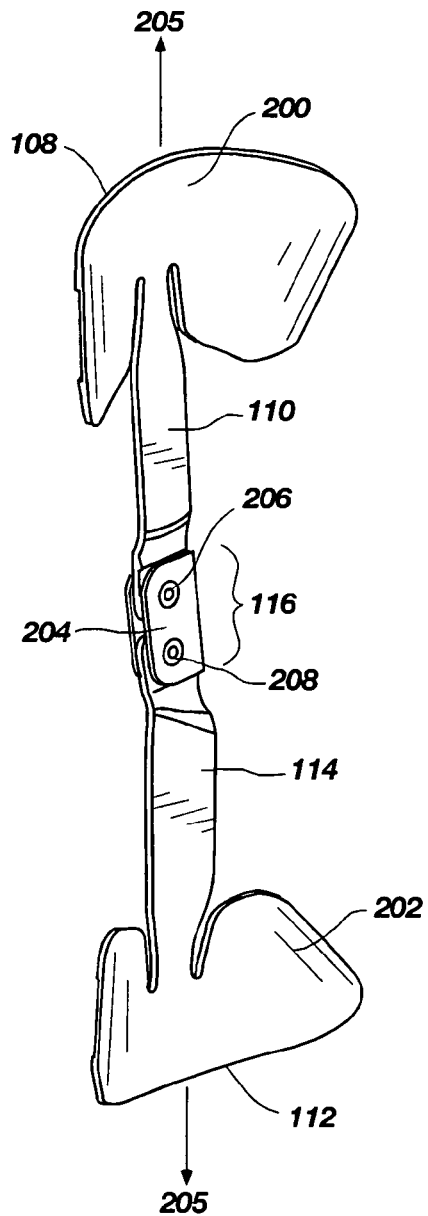
FIG. 2A
FIG. 2B

ORTHOTIC APPARATUS

BACKGROUND

A variety of knee braces are currently available for treating different knee problems. Knee braces may be designed to impart forces on limbs surrounding the knee to relieve compressive forces in a portion of the knee. Additionally, knee braces are often employed to support the knee after a knee injury, such as a sprain, or to assist with rehabilitation of the knee after a traumatic event, such as knee surgery.

The human knee is a joint held together by small, powerful ligaments. The femur (i.e., the thighbone) meets the tibia (i.e., the large shin bone) to form the main knee joint called the femoro-tibial joint. The kneecap (i.e., the patella) joins the femur to form a second joint called the femoro-patellar joint. The patella protects the front of the knee. The knee is surrounded by a joint capsule with collateral ligaments strapping the inside and outside of the joint and cruciate ligaments crossing within the joint. The collateral ligaments run along the sides of the knee and limit the sideways motion of the knee. The anterior cruciate ligament ("ACL") connects the tibia to the femur at the center of the knee and functions to limit rotation and forward motion of the tibia. The ACL divides the knee into an inner (medial) and an outer (lateral) compartment. The posterior cruciate ligament ("PCL") is located aft of the ACL and limits backward motion of the tibia. The knee also includes a thickened cartilage pad known as a meniscus attached to the tibia and an articular cartilage attached to the femur. The meniscus and articular cartilage function as smooth bearing surfaces that allow for pain-free relative rotation of the femur and tibia.

Despite the knee being held together by powerful ligaments, the knee is still a relatively weak joint that can be easily damaged. For example, the knee may be damaged by participating in sporting events, overloading due to obesity, aging, or misalignment of the knee. Most knee problems are a result of damage of the cartilage of the knee and strain of the ligaments of the knee.

One important knee problem is unicompartmental osteoarthritis in which either the medial (inward) or the lateral (outward) compartment of the knee joint is deteriorated. In a proper functioning knee, both compartments are loaded generally uniformly. A knee joint that suffers from unicompartmental osteoarthritis is characterized by an uneven distribution of pressure in either the medial or lateral compartment of the knee. Such uneven distribution of pressure can wear away the smooth cartilage lining the inside of the knee, which may, consequently, lead to painful, direct contact between the femur and the tibia.

Unicompartmental osteoarthritis may be treated by using a knee brace that is configured to urge the femur and tibia apart in the affected compartment of the knee to reduce or eliminate the painful bone-to-bone contact between the femur and the tibia. However, many conventional knee braces employ complicated mechanisms for applying a load that urges the femur and tibia apart. Despite the availability of such conventional knee braces to treat unicompartmental osteoarthritis, there is still a need for an improved knee brace to treat unicompartmental arthritis in a knee or other joint.

SUMMARY

Embodiments of the invention relate to an orthotic apparatus. In one embodiment of the invention, an orthotic apparatus includes a frame structure having an upper frame portion moveable relative to a lower frame portion. The orthotic apparatus further includes at least one strap attached to the upper frame portion and the lower frame portion of the frame structure. The at least one strap and the frame structure, together, are configured to apply a therapeutic moment to a joint of a limb responsive to positioning the limb within a limb-receiving space formed between the at least one strap and the frame structure.

According to another embodiment of the invention, in use, a limb may be positioned within a limb-receiving space formed between a frame structure and at least one strap attached thereto of an orthotic apparatus. The limb may be engaged with the frame structure and the at least one strap to tension the at least one strap and apply a therapeutic moment to a joint of the limb.

BRIEF DESCRIPTION OF THE DRAWINGS

The drawings illustrate several embodiments of the invention, wherein like reference numerals refer to like or similar elements in different views or embodiments shown in the drawings.

FIG. 2A is a front perspective view of the frame structure shown in FIGS. 1A-1C according to one embodiment of the invention.

FIG. 2B is a rear perspective view of the frame structure shown in FIG. 2A.

DETAILED DESCRIPTION

Embodiments of the invention relate to an orthotic apparatus including a frame structure having at least one strap attached thereto, with the frame structure and the at least one strap configured to apply a therapeutic moment to a joint of a user's limb responsive to the user donning the orthotic apparatus. The disclosed orthotic apparatus embodiments are configured to apply a therapeutic moment to, for example, a user's knee for alleviating pressure in a lateral or medial compartment of the knee for treating osteoarthritis of the knee, for alleviating other knee infirmities, or for generally supporting the knee.

Figure 1A:
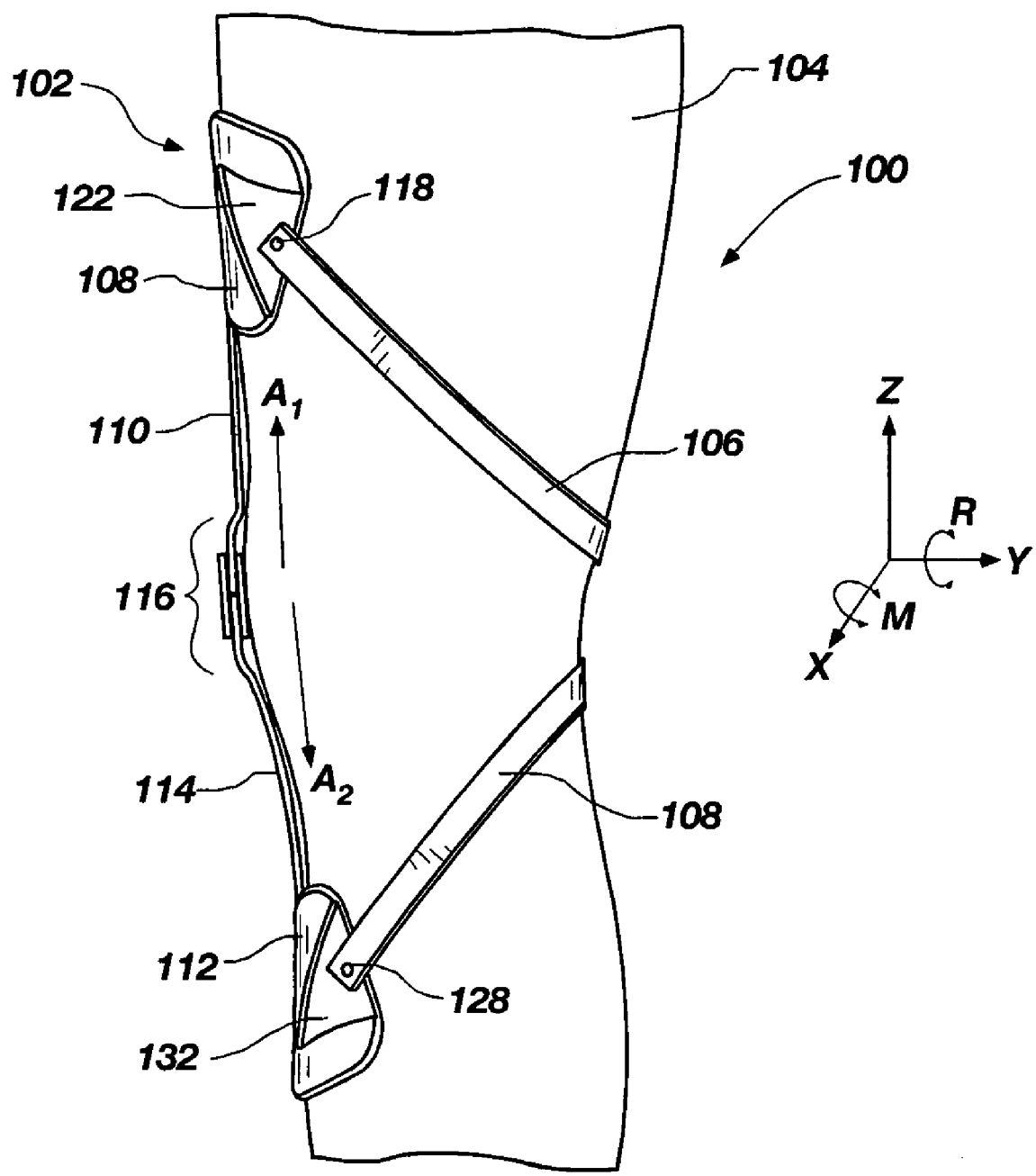
FIG. 1A is a perspective view taken from a back side of a user's leg illustrating an orthotic apparatus having a frame structure positioned on a medial side of a knee and straps configured to apply a therapeutic load to the knee according to one embodiment of the invention.
Figure 1B:
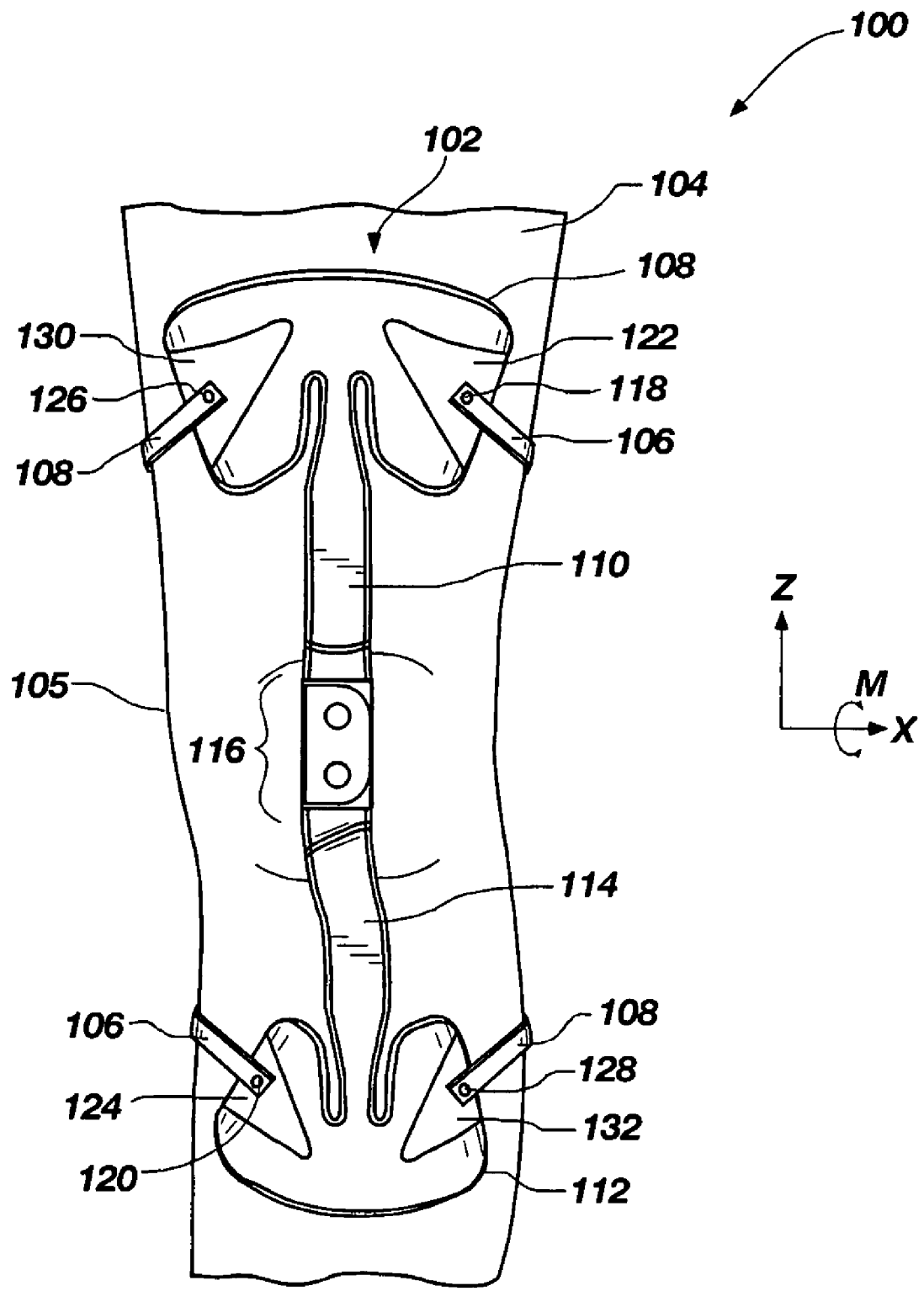
FIG. 1B is a perspective view of the orthotic apparatus shown in FIG. 1A taken from the medial side of the knee.
Figure 1C:
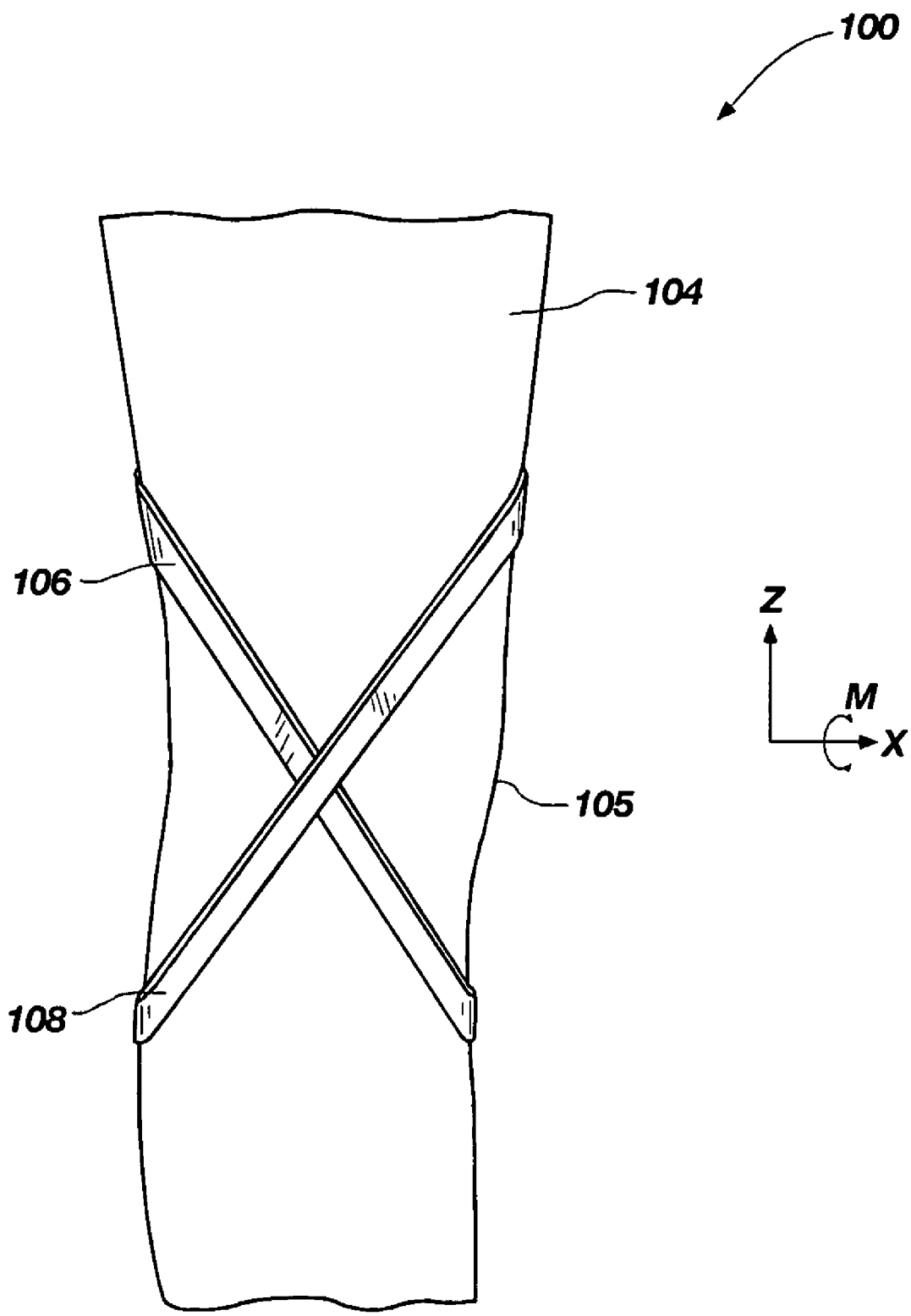
FIG. 1C is a perspective view of the orthotic apparatus shown in FIG. 1A taken from a lateral side of the knee.

FIGS. 1A-1C are perspective views of an orthotic apparatus 100 taken from a back side, a medial side, and a lateral side, respectively of a user's leg according to one embodiment of the invention. The orthotic apparatus 100 includes a frame structure 102 extending along a length of a leg 104 of the user, with the frame structure 102 positioned adjacent to a medial side of the user's knee 105. As will be discussed in more detail below, straps 106 and 108 are connected to the frame structure 102, and the straps 106 and 108 in conjunction with the frame structure 102 are configured to apply a therapeutic moment M to the knee 105 of the user's leg 104 upon the user donning the straps 106 and 108 and the frame structure 102. Thus, the therapeutic moment M is not applied to the knee 105 using a complicated, costly, and possibly defect prone device (e.g., a ratchet mechanism) configured to tension the straps 106 and 108 or by the user manually tensioning the straps 106 and 108.

The frame structure 102 includes an upper shell 108 that may be configured to generally conform to the user's leg 104 and an elongated support arm 110 extending from the upper shell 108. The frame structure 102 further includes a lower shell 112 that may also configured to generally conform to the user's leg 104 and an elongated support arm 114 extending toward the elongated support arm 108. The elongated support arms 110 and 114 are hingedly connected to each other via a hinge assembly 116 to enable rotation relative to each other in a direction R when the user bends the knee 105.

The elongated support arms 110 and 114 and the shells 108 and 112 may be formed from a number of different materials, such as engineering plastics, metallic materials, polymer-matrix composites, or another suitable material. In the illustrated embodiment, the elongated support arms 110 and 114 are integrally formed with the corresponding upper shell 108 and lower shell 112. However, in other embodiments of the invention, the elongated support arms 110 and 114 and the shells 108 and 112 may be separate pieces, with the upper shell 108 attached to the elongated support arm 110 and the lower shell 112 attached to the elongated support arm 114 using fasteners or another suitable technique.

Figure 2C:
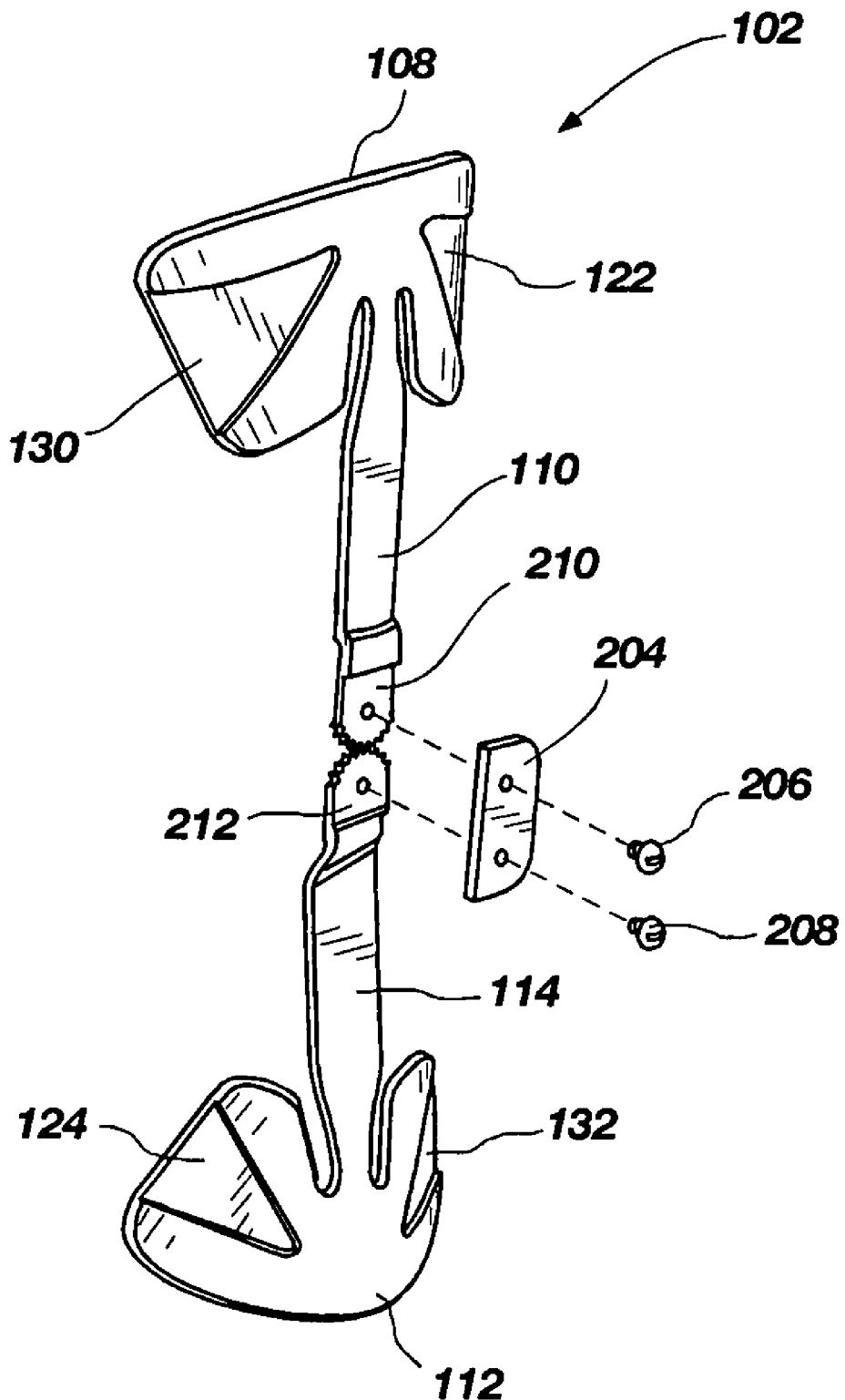
FIG. 2C is an exploded perspective view of the frame structure shown in FIGS. 2A and 2B that illustrates the hinge assembly of the frame structure in more detail.

FIGS. 2A-2C are front, rear, and exploded perspective views of the frame structure 102 and hinge assembly 116 that shows the configuration thereof in more detail. As previously noted, the upper shell 108 and the lower shell 112 may be configured to conform to the user's leg 104. As best shown in FIG. 2B, the upper shell 108 has a surface 200 and the lower shell 112 has a surface 202, each of which may be suitably concavely curved to enable conforming to the user's leg 104. As best shown in FIG. 2C, the hinge assembly 116 includes a coupling member 204 that may partially enclose a gear 210 located at a distal end of the elongated support arm 110, and a gear 212 located at a distal end of the elongated support arm 114. The coupling member 204 is secured to the elongated support arms 110 and 114 using fasteners 206 and 208 that are secured to the gears 210 and 212 and the coupling member 204. When assembled, the gears 210 and 212 mesh with each other. As previously discussed, the hinge assembly 116 enables the elongated support arms 110 and 114 to be relatively rotated in the direction R (See FIG. 1A) about an axis generally perpendicular to a longitudinal axis 205 of the frame structure 102. The elongated support arm 110 rotates about an axis (not shown) that passes through the fastener 206 and the elongated support arm 114 rotates about an axis (not shown) that passes through the fastener 208.

It is noted that the frame structure 102 merely represents one embodiment of a suitable frame structure for the orthotic apparatus 100. Any suitable frame structure that is configured to rotate or bend with rotation of the user's knee 105 when the frame structure is secured to the user's leg 104 may be used. For example, the gears 210 and 212 may be omitted and the elongated support arms 108 and 112 may be pivotally connected to each other using a fastener. Additionally, in a further embodiment of the invention, the gears 210 and 212 and the hinge assembly 116 may be omitted. In such an embodiment, the frame structure 102 may be a unitary piece that is configured to flex or bend with a selected stiffness as the user bends their knee 105. Thus, in such an embodiment, the upper shell 108 and elongated support arm 110 may move relative to the lower shell 112 and elongated supper arm 114 when the user bends their knee 105. Furthermore, in any of the embodiments of the invention disclosed herein, a fabric compression sleeve (not shown) may be provided that conceals the frame structure 102 and/or is attached to the frame structure 102, for example, using Velcro® straps or another suitable securing structure. The fabric compression sleeve may help properly position and maintain the position of, during use, the frame structure 102 on the leg 104 of the user and further provide a therapeutic benefit of compressing muscles surrounding the knee 105.

Turning again to FIGS. 1A-1C, the straps 106 and 108 of the orthotic apparatus 100 are each attached to the upper shell 108 and the lower shell 112 so that they cross each other to form an X-type pattern as best shown in FIG. 1C. The strap 106 includes a proximal end 118 and a distal end 120, with the proximal end 118 attached to side portion 122 of the upper shell 108 and the distal end 120 attached to side portion 124 (FIG. 1B) of the lower shell 112. The strap 108 includes a proximal end 126 and a distal end 128, with the proximal end 126 attached to side portion 130 of the upper shell 108 and the distal end 128 attached to side portion 132 (FIG. 1B) of the lower shell 112. For example, each strap 106 and 108 may be attached to the upper shell 108 and lower shell 112 using screws, rivets, buttons, or another suitable fastening mechanism. It is noted that while two straps 106 and 108 are employed in the illustrated embodiment, in other embodiments of the invention, a single strap may be coiled in figure-eight type of pattern so that the single strap crosses over itself in a manner similar to the X-type pattern shown in FIG. 1C.

Each strap 106 and 108 may be made from an elastic material. For example, the elastic material may have an elastic limit of about 1 percent to about 40 percent. Suitable elastic materials include, but are not limited to, polymeric materials (e.g., elastomeric polymers, nylon, or rubber) and elastic fabrics (e.g., Lycra®, braided elastic materials, woven elastic materials, knitted elastic materials, or corded elastic materials). As will be discussed in more detail below, by selecting the elastic stiffness of each strap 106 and 108, the stiffness of the frame structure 102, and the amount of physical interference between the user's leg 104 when the user inserts their leg 104 into the orthotic apparatus 100, the magnitude of the therapeutic moment M applied to the knee 105 may be tailored.

Figure 3B:
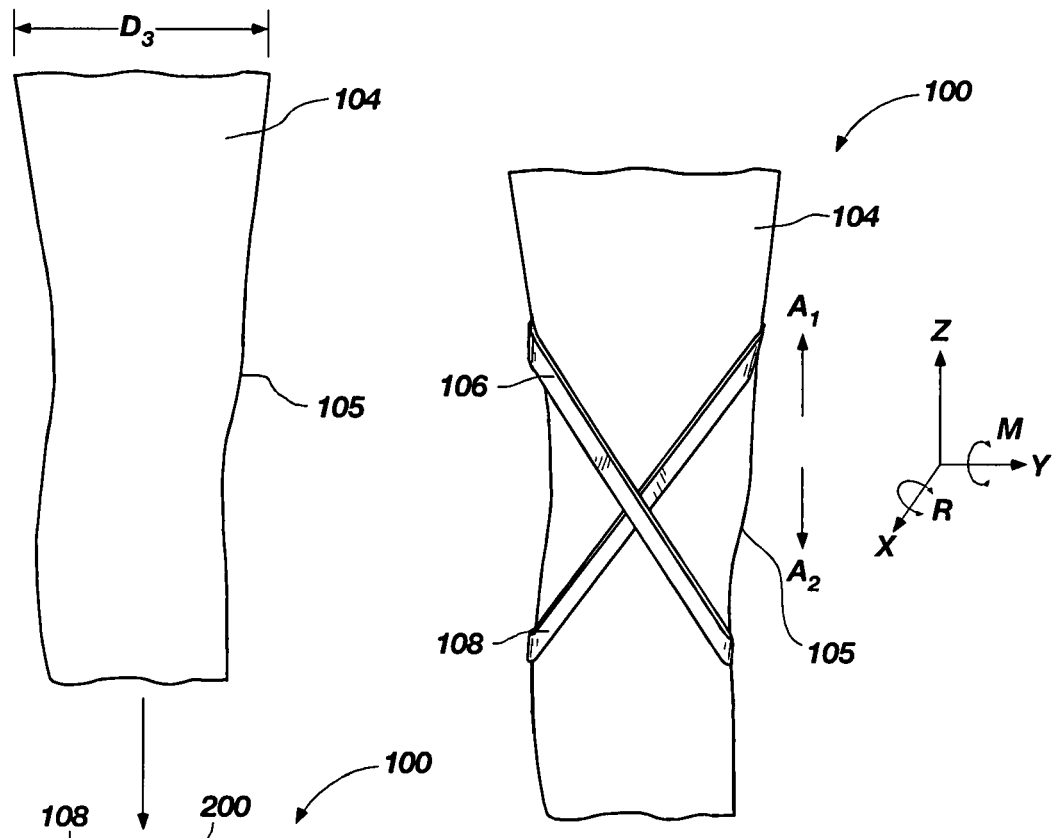
FIG. 3B is a perspective view of the orthotic apparatus shown in FIG. 1A taken from a lateral side of the knee after insertion of the leg of the user into the limb-receiving space.
Figure 3A:
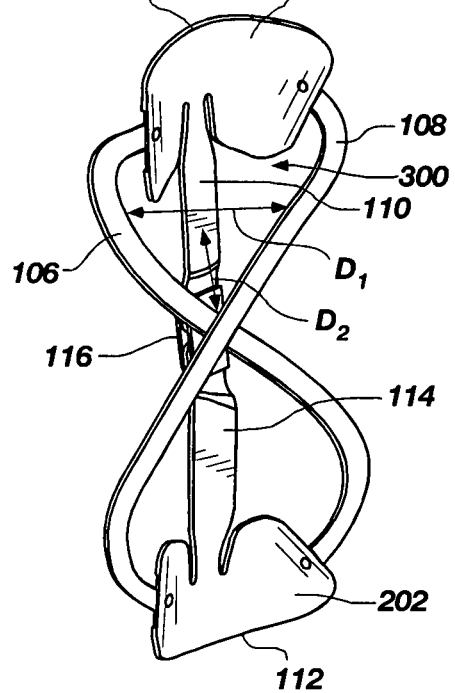
FIG. 3A is a perspective view of the orthotic apparatus shown in FIGS. 1A-1C illustrating a leg of a user being inserted into a limb-receiving space of the orthotic apparatus.

The manner in which the orthotic apparatus 100 applies the therapeutic moment M to the knee 105 of the leg 104 is best understood with reference to FIGS. 3A and 3B. In use, the user dons the orthotic apparatus 100 by inserting their leg 104 into a limb-receiving space 300 defined between the frame structure 102 and the straps 106 and 108. The limb-receiving space 300 may be defined by one or more lateral dimensions. For example, in the illustrated embodiment shown in FIG. 3A, the limb-receiving space 300 is defined by a first lateral dimension $D_1$ extending between the straps 106 and 108 and a second lateral dimension $D_2$ extending between the frame structure 102 and the strap 104. Depending upon the manner in which the straps 106 and 108 are configured and attached to the frame structure 102, the first and second lateral dimensions $D_1$ and $D_2$ may be approximately equal to each other and, in other embodiments, may be different. The leg 104 of the user exhibits a lateral dimension or diameter $D_3$ that is greater than the first lateral dimensions $D_1$, second lateral dimension $D_2$, or both. Due to the lateral dimension or diameter $D_3$ of the leg 104 being greater than at least one of the first and second lateral dimensions $D_1$ and $D_2$ of the limb-receiving space 300, the leg 104 physically interferes with the frame structure 102 and the straps 106 and 108 so that the straps 106 and 108 become tensioned as the user inserts their leg 104 into the limb-receiving space 300. Referring to FIG. 3B, tensioning the straps 106 and 108 enables the straps 106 and 108 in conjunction with the frame structure 102 (e.g., the upper shell 108 and lower shell 112 bearing against the leg 104) to subject the knee 105 to a generally three-point bending loading that applies a moment M to the knee 105 of the user. The upper shell 108 and lower shell 112 function as two of the points and the point or region of the straps 106 and 108 that cross each other functions as the third point. Thus, the moment M is not applied to the knee 105 using a device configured to tension the straps 106 and 108 or by the user manually tensioning the straps 106 and 108. Instead, the act of the user donning the orthotic apparatus 100 results in the moment M being applied to the knee 105 of the user.

The moment M illustrated in FIGS. 1A-1C and 3B is a valgus moment that urges the femur and tibia apart generally in directions $A_1$ and $A_2$, respectively, to unload the affected medial compartment of the knee 105. Of course, the orthotic apparatus 100 may be positioned with the frame structure 102 on a lateral side of the user's knee 105. In such a case, donning the orthotic apparatus 100 applies a varus moment to the user's knee 105 and urges the femur and tibia apart on the affected lateral compartment of the knee 105 of the user.

In FIGS. 1A-3B, the straps 106 and 108 are illustrated as being non-adjustable, with the distal ends 118, 126 and proximal ends 120, 128 thereof attached to the frame structure 102. In other words, the locations that the straps 106 and 108 attach to the frame structure 102 are fixed. However, in other embodiments of the invention, the frame structure 102 and the straps 106 and 108 may be configured to allow the location that the distal ends 118, 126 and proximal ends 120, 128 of the thereof attach to the frame structure 102. Such embodiments enable slightly changing the volume of a limb-receiving space (e.g., the limb-receiving space 300 of the orthotic apparatus 100) so that a range of user limb sizes can be accommodated and, further enable tailoring a magnitude of a moment applied to a user's knee upon donning the orthotic apparatus. For example, for a given user leg size and strap configurations, reducing the volume of the limb-receiving space will increase the magnitude of the moment applied to the user's knee.

Figure 4:
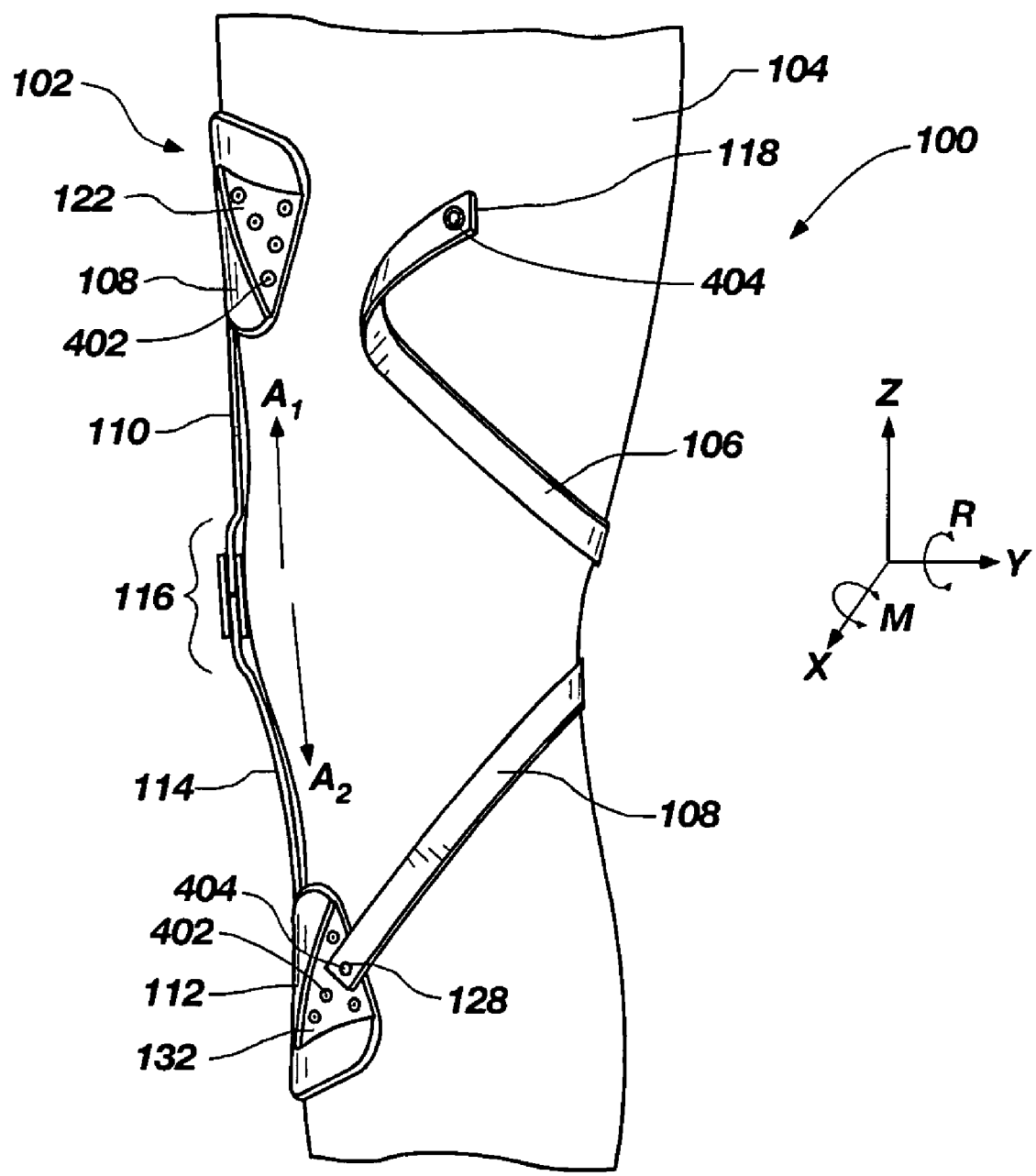
FIG. 4 is a perspective view of an orthotic apparatus configured to allow for the location that the straps attach to the frame structure to be slightly adjusted according to another embodiment of the invention.

FIG. 4 is a perspective view of an orthotic apparatus 400 that allows the location that the straps 106 and 108 attach to the frame structure 102 to be slightly adjusted according to another embodiment of the invention. The orthotic apparatus 400 is structurally similar to the orthotic apparatus 100 shown in FIGS. 1A-1C. Therefore, in the interest of brevity, components in both orthotic apparatuses 100 and 400 that are identical to each other have been provided with the same reference numerals, and an explanation of their structure and function will not be repeated unless the components function differently in the substrate holders 100 and 400. The frame structure 102 further includes a plurality of spaced buttons 402 (or other attachment member) mounted to upper shell 108 on the side portions 122 and 130 (not shown) thereof and to the lower shell 112 on the side portions 124 and 132 (not shown) thereof. The proximal and distal ends 118, 120 of the strap 106 may each include at least one button 404 (or other attachment member) configured to releasably attach (e.g., snap fit) to each of the buttons 402, and proximal and distal ends 126, 128 of the strap 108 may each include at least one button 404 (or other attachment member) also configured to releasably attach to each of the buttons 402. Thus, as desired or needed for a particular user's leg size, the position that the straps 106 and 108 attach to the frame structure 102 may be adjusted by selecting, for example, which one of the buttons 402 mounted to the side portion 122 that the button 404 of the proximal end 118 of the strap 106 snap fits with.

In other embodiments of the invention, only one of the straps 106 and 108 may be configured to releasably attach to the frame structure 102. In further embodiments of the invention, at least one end of at least one of the straps 106 and 108 may include more than one of the buttons 404. For example, the proximal end 118 and distal end 120 of the strap 106 may each include more than one of the buttons 404 and the side portions 122 and the side portions 124 may each include only one of the buttons 402.

Although the invention has been disclosed and described by way of some embodiments, it is apparent to those skilled in the art that several modifications to the described embodiments, as well as other embodiments of the invention are possible without departing from the spirit and scope of the invention.

The invention claimed is:

1. An orthotic apparatus, comprising:
   a frame structure including an upper frame portion moveable relative to a lower frame portion;
   at least one strap including two or more ends, the two or more ends of the at least one strap attached to the upper frame portion and the lower frame portion of the frame structure, each and every one of the two or more ends of the at least one strap is attached to the frame structure by at least one of a screw, a rivet, or a button;
   the at least one strap and the frame structure, together, are configured to apply a therapeutic moment to a joint of a limb responsive to positioning the limb within a limb-receiving space formed between the at least one strap and the frame structure; and
   wherein a device operable to tension the at least one strap is not included.

2. The orthotic apparatus of claim 1 wherein the at least one strap and the frame structure are configured so that a position that the at least one strap attaches to the frame structure is relatively adjustable.

3. The orthotic apparatus of claim 1 wherein the at least one strap and the frame structure are configured so that a position that the at least one strap attaches to the frame structure is non-adjustable.

4. The orthotic apparatus of claim 1 wherein the at least one strap exhibits an elastic limit of about 1 percent to about 40 percent.

5. The orthotic apparatus of claim 1 wherein the at least one strap comprises an elastomeric material.

6. The orthotic apparatus of claim 1 wherein the at least one strap comprises an elastic fabric.

7. The orthotic apparatus of claim 1 wherein the at least one strap comprises only one strap.

8. The orthotic apparatus of claim 1 wherein:
   the upper frame portion comprises an upper shell having a first elongated support arm extending therefrom;
   the lower frame portion comprises a lower shell having a second elongated support arm extending therefrom that is hingedly connected to the first elongated support arm; and
   the at least one strap comprises first and second straps each of which is attached to the upper shell and the lower shell in a manner so that the first strap and the second strap cross each other.

9. The orthotic apparatus of claim 1 wherein the upper frame portion and the lower frame portion are rotatable relative to each other.

10. A method, comprising:
 positioning a limb within a limb-receiving space formed between a frame structure and at least one strap attached thereto of an orthotic apparatus;
 engaging the limb with the frame structure and the at least one strap to tension the at least one strap and apply a therapeutic moment to a joint of the limb without manually tensioning the at least one strap using a device operable to tension the at least one strap; and
 relatively adjusting at least one position at which the at least one strap attaches to the frame structure.

11. The method of claim 10 wherein positioning a limb within a limb-receiving space formed between a frame structure and at least one strap attached thereto of an orthotic apparatus comprises:
 inserting the limb within the limb-receiving space.

12. The method of claim 10 wherein positioning a limb within a limb-receiving space formed between a frame structure and at least one strap attached thereto of an orthotic apparatus comprises:
 positioning a knee of a subject within a limb-receiving space.

13. The method of claim 10 wherein engaging the limb with the frame structure and the at least one strap to tension the at least one strap and apply a therapeutic moment to a joint of the limb comprises:
 physically interfering the limb with the frame structure and the at least one strap as a result of at least one lateral dimension of the limb being greater than at least one lateral dimension of the limb-receiving space prior to positioning of the limb therein.

14. The method of claim 10 wherein the act of engaging the limb with the frame structure and the at least one strap tensions the at least one strap and applies the therapeutic moment substantially simultaneously.

15. The method of claim 10 wherein the at least one strap comprises first and second straps each of which is attached to the frame structure.

16. The method of claim 10 wherein the at least one strap comprises only one strap.

17. The method of claim 10 wherein the at least one strap comprises an elastomeric material.

18. The method of claim 10 wherein the at least one strap comprises an elastic fabric.

19. The method of claim 10 wherein each and every end of the at least one strap is fastened to the frame structure by at least one of a screw, a rivet, or a button.

20. An orthotic apparatus, comprising:
 a frame structure including an upper frame portion moveable relative to a lower frame portion;
 at least one strap including two or more ends, the two or more ends of the at least one strap attached to the upper frame portion and the lower frame portion of the frame structure, each and every one of the two or more ends of the at least one strap is attached to the frame structure by a means for fastening
 the at least one strap and the frame structure, together, are configured to apply a therapeutic moment to a joint of a limb responsive to positioning the limb within a limb-receiving space formed between the at least one strap and the frame structure;
 wherein the at least one strap is configured to increase in length responsive to insertion of the limb into the limb-receiving space so that the limb-receiving space can accommodate a range of limb sizes; and
 wherein a device operable to tension the at least one strap is not included.

21. The orthotic apparatus of claim 20 wherein the means for fastening comprises at least one of a screw, a rivet, or a button.

22. An orthotic apparatus, comprising:
 a frame structure including an upper frame portion moveable relative to a lower frame portion;
 at least one strap including two or more ends, the two or more ends of the at least one strap attached to the upper frame portion and the lower frame portion of the frame structure, each and every one of the two or more ends of the at least one strap is attached to the frame structure by at least one of a screw, a rivet, or a button;
 the at least one strap and the frame structure, together, are configured to apply a therapeutic moment to a joint of a limb responsive to positioning the limb within a limb-receiving space formed between the at least one strap and the frame structure;
 wherein the at least one strap exhibits an elastic limit of about 1 percent to about 40 percent; and
 wherein a device operable to tension the at least one strap is not included.

23. The orthotic apparatus of claim 22 wherein the at least one strap comprises an elastomeric material.

24. The orthotic apparatus of claim 22 wherein the at least one strap comprises an elastic fabric.

25. A method, comprising:
 positioning a limb within a limb-receiving space formed between a frame structure and at least one strap attached thereto of an orthotic apparatus;
 engaging the limb with the frame structure and the at least one strap to tension the at least one strap and apply a therapeutic moment to a joint of the limb without manually tensioning the at least one strap using a device operable to tension the at least one strap; and
 adjusting a position that the at least one strap is attached to the frame structure to alter a volume of the limb-receiving space prior to engaging the limb with the frame structure and the at least one strap to tension the at least one strap.

* * * * *